US00PP18339P2

(12) United States Plant Patent
Hammett

(10) Patent No.: US PP18,339 P2
(45) Date of Patent: Dec. 18, 2007

(54) ***DAHLIA* PLANT NAMED 'KNOCKOUT'**

(50) Latin Name: *Dahlia variabilis*
Varietal Denomination: Knockout

(76) Inventor: Keith Hammett, 488 C Don Buck Road, Auckland 1008 (NZ)

( * ) Notice: Subject to any disclaimer, the term of this patent is extended or adjusted under 35 U.S.C. 154(b) by 15 days.

(21) Appl. No.: 11/501,509

(22) Filed: Aug. 8, 2006

(30) Foreign Application Priority Data

Aug. 25, 2005 (NZ) ..... DAH015

(51) Int. Cl.
*A01H 5/00* (2006.01)

(52) U.S. Cl. ..... Plt./321

(58) Field of Classification Search ..... Plt./321
See application file for complete search history.

*Primary Examiner*—Kent Bell

(57) ABSTRACT

A new cultivar of *Dahlia* named 'KNOCKOUT' that is distinguishable by upright habit, mahogany-black divided leaves, and yellow star-shaped blossoms. In combination these traits set 'KNOCKOUT' apart from all other existing varieties of *Dahlia* known to the inventor.

2 Drawing Sheets

Genus: *Dahlia*. Species: *variabilis*.
Denomination: 'KNOCKOUT'.

BACKGROUND OF THE INVENTION

The present invention relates to a new and distinct cultivar of *dahlia* that is grown for use in mixed combinations, beds and the landscape. The new invention is known botanically as *Dahlia variabilis* and will be referred to hereinafter by the cultivar name 'KNOCKOUT'. The specific epithet *variabilis* represents a hybrid seedling line that came from crossing various original wild species in the early 1800's, and refers to the species' wide range of flower color and shapes. *Dahlia* is in the family *Compositae*. The inflorescence of 'KNOCKOUT' is a "single" form blossom and exhibits a single row of ray florets surrounding a central cluster of disk florets.

'KNOCKOUT' was selected by the inventor as a seedling that resulted from the controlled cross-pollination carried out by the inventor in a cultivated area of Auckland, New Zealand. The breeding began in 2001 by crossing an individual unpatented *Dahlia variabilis* named 71157/01 as the female parent and an individual *Dahlia variabilis* from the inventor's experimental F1 Lines as the male parent. The female parent was planted in associated with dahlia plants that exhibited similar characteristics. Seed was collected from the female parent and coded as 71334/01, then sown with the intention of making a selection from the seedlings that resulted.

'KNOCKOUT' was selected in 2002 based on the criteria of leaf color and clarity of flower color. Selection was conducted by the inventor, in Auckland, New Zealand. The unique traits that distinguish the new *Dahlia* variety named 'KNOCKOUT' from other varieties of the same genus are mahogany-black divided leaves and profusions of vivid yellow star-shaped blossoms. The new *Dahlia* named 'KNOCKOUT' is distinguishable from the parents by the clarity of bloom color and darkness of the leaves.

'KNOCKOUT' exhibits upright habit, large mahogany-black buds, fragrant yellow inflorescences, and mahogany-black foliage. The large star-shaped blossoms bloom in summer and fall. Cultural conditions include full sun, regular water and rich well-draining potting soil. 'KNOCKOUT' is hardy to USDA Zone 8 and grows to 0.9 m in height and 0.9 m in width at maturity.

The first asexual reproduction of 'KNOCKOUT' was conducted in 2004 in Auckland, New Zealand. The method of asexual propagation utilized was tissue culture. Since that time under careful observation, the distinguishing characteristics have been determined stable, uniform, and to be reproduced true to type in subsequent generations of asexual propagation.

SUMMARY OF THE INVENTION

The following traits have been repeatedly observed and represent the distinguishing characteristics of the new *Dahlia* cultivar named 'KNOCKOUT'. These traits in combination distinguish 'KNOCKOUT' from all other existing varieties of *Dahlia* known to the inventor. 'KNOCKOUT' has not been tested under all possible conditions and phenotypic differences may be observed with variations in environmental, climatic, and cultural conditions, however, without any variance in genotype.

1. 'KNOCKOUT' exhibits upright habit.
2. 'KNOCKOUT' exhibits mahogany-black divided leaves.
3. 'KNOCKOUT' is grown for use in mixed combinations, beds and the landscape.
4. 'KNOCKOUT' exhibits large mahogany-black buds and dark purple stems.
5. 'KNOCKOUT' exhibits fragrant vivid yellow star-shaped blossoms.
6. 'KNOCKOUT' blooms summer and fall.
7. 'KNOCKOUT' grows to 0.9 m in height and 0.9 m in width at maturity.
8. 'KNOCKOUT' is hardy to USDA Zone 8.

BRIEF DESCRIPTION OF THE DRAWINGS

The accompanying color drawings labeled

The drawing labeled FIG. 1 depicts the entire plant in bloom.

The drawing labeled FIG. 2 depicts a close-up view of the inflorescences of buds.

Figure 1:
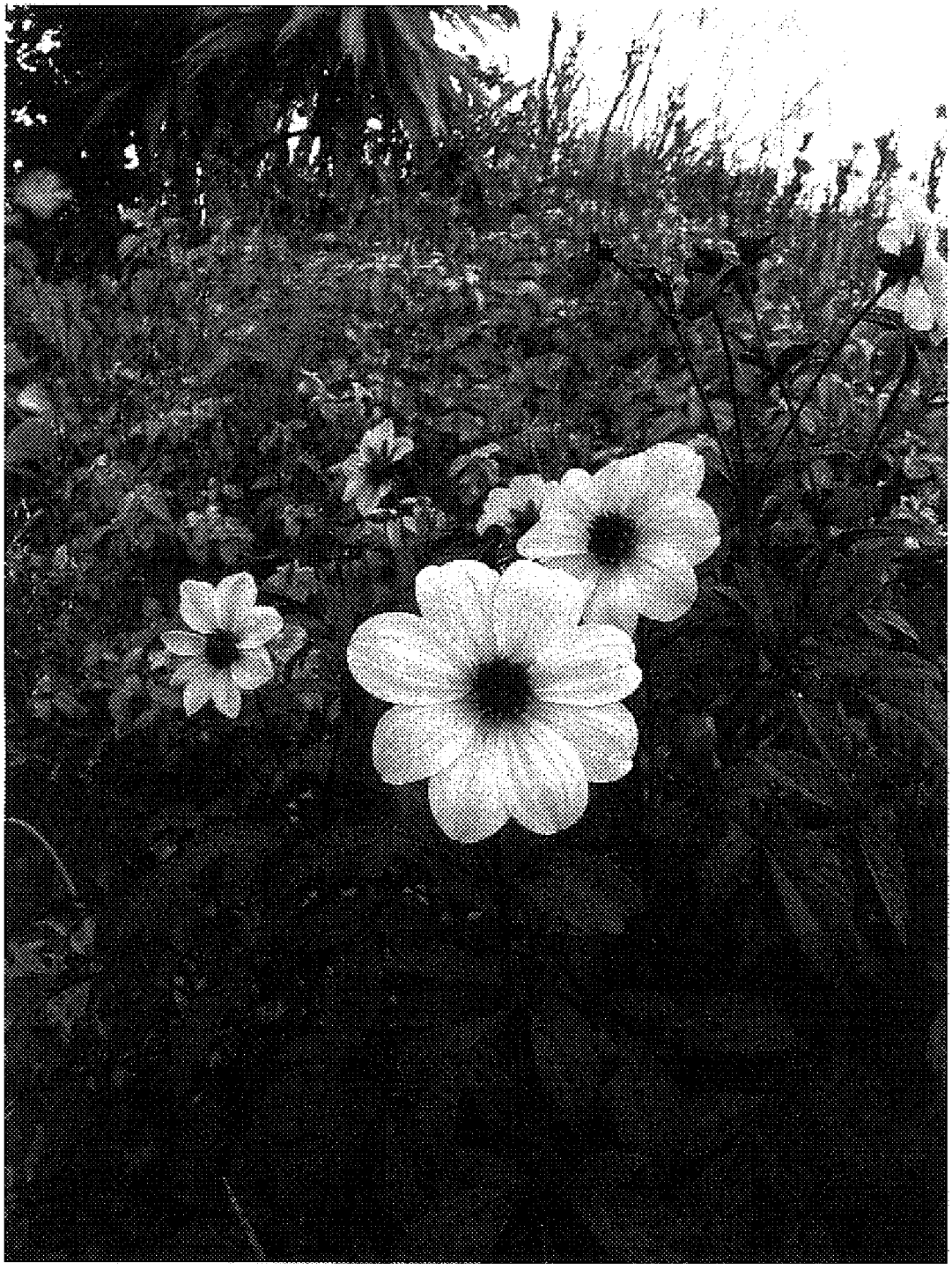
FIG. 1 and FIG. 2 illustrate the overall appearance of the new *Dahlia* cultivar named 'KNOCKOUT' showing the colors as true as is reasonably possible to obtain in colored reproductions of this type. Colors in the photographs may differ from the color values cited in the detailed botanical description, which accurately describes the actual colors of the new *Dahlia* variety named 'KNOCKOUT'.
Figure 2:
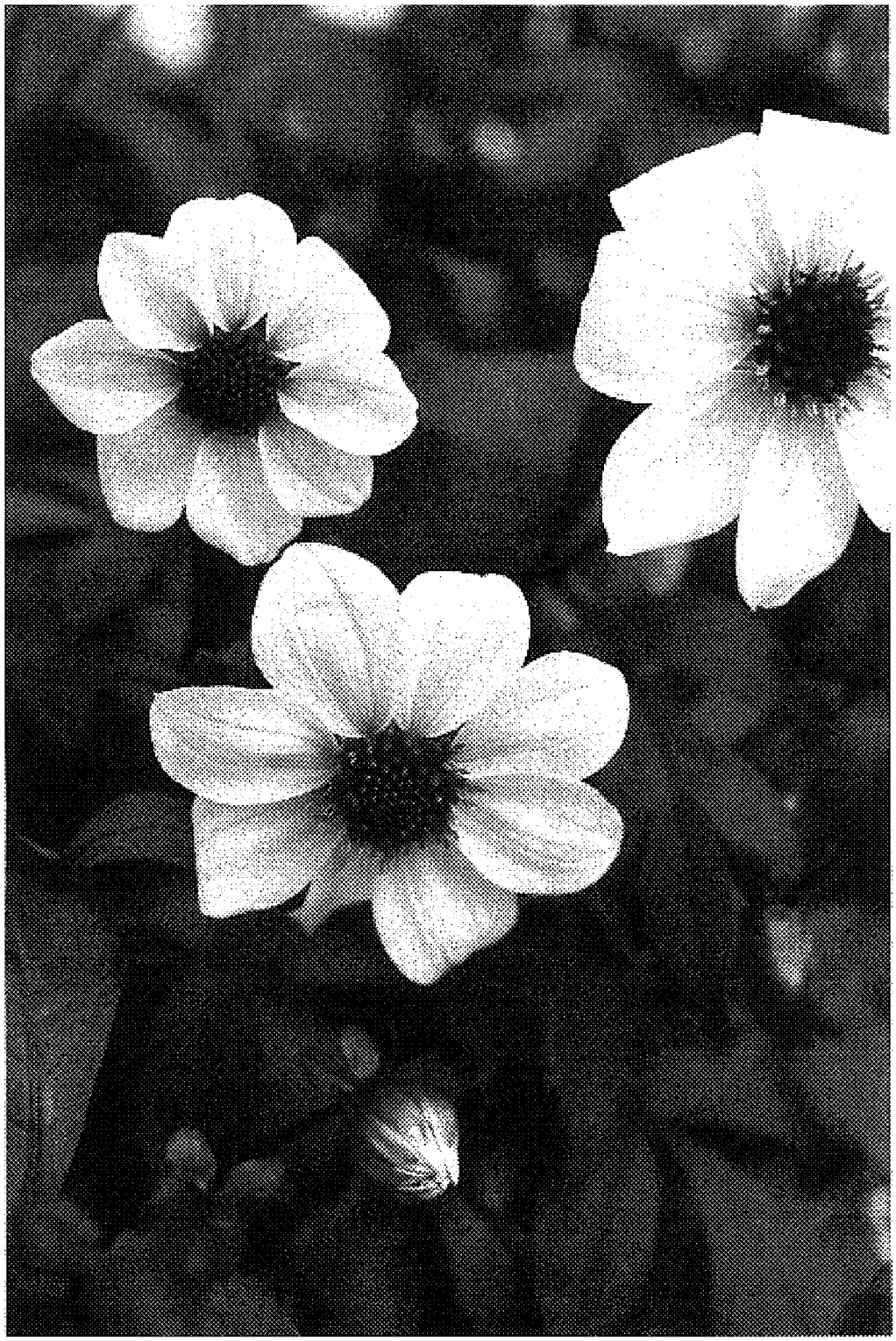

Drawings were made using conventional techniques and although inflorescence and foliage color may appear different from actual color due to light reflectance, they are as accurate as possible by conventional photography.

BOTANICAL DESCRIPTION OF THE PLANT

The following is a detailed botanical descriptions of the new *Dahlia* cultivar named 'KNOCKOUT'. Observations, measurements, values and comparisons were collected in Arroyo Grande, Calif. from 2-liter container plants. Color determinations were made in accordance with the 2001 Royal Horticultural Society Colour Chart from London England, except where general color terms of ordinary dictionary significance are used. Growing requirements are similar to the species.

Botanical classification: *Dahlia variabilis* 'KNOCKOUT'.
Family: Compositae.
Genus: *DAHLIA*.
Species: *variabilis*.
Denomination: 'KNOCKOUT'.
Common name: *Dahlia*.
Parentage: *Dahlia variabilis* 'KNOCKOUT' is a whole seedling plant that resulted from the deliberate controlled cross-pollination of the following parents:
- *Female parent.*—An individual plant of *Dahlia variabilis* named 71157/01.
- *Male parent.*—An individual plant of *Dahlia variabilis* from experimental F1 Lines.

Propagation method: Fine and fibrous.
Rooting system: Fine and fibrous.
Vigor: Vigorous.
Habit: Upright habit.
Use: For use in mixed combinations, beds and the landscape.
Type: Perennial.
Dimensions in first season: 0.6 m. in height and 0.6 m. in width.
Dimensions at maturity: 0.9 m. in height and 0.9 m. in width.
Cultural requirements: Grow in full sun with regular water, and well-draining potting soil.
Pest susceptibility: Susceptible to aphids.
Disease susceptibility: Susceptible to mildew in highly humid conditions.
Hardiness: USDA Zone 8.
Stem:
- *Color.*—N186B.
- *Dimensions.*—45 cm in length and 0.4 cm in width.
- *Shape.*—Cylindrical.
- *Surface.*—Glabrous.
- *Internode length* (*average*).—7 cm.

Foliage:
- *Type.*—Evergreen.
- *Leaf arrangement.*—Opposite.
- *Leaf division.*—Simple.
- *Leaf dimensions* (*average*).—11.50 cm in length and 9 cm in width.
- *Leaf color* (*adaxial surface*).—N186A.
- *Leaf color* (*abaxial surface*).—189A.
- *Margin.*—Ciliate and pinnitisect.
- *Leaf shape.*—Hastate.
- *Leaf base.*—Attenuate.
- *Leaf apex.*—Apiculate.
- *Leaf venation pattern.*—Pinnate.
- *Vein color* (*abaxial and adaxial surfaces*).—N186C.
- *Leaf surfaces* (*abaxial surfaces*).—Slightly puberulent.
- *Leaf surfaces* (*adaxial surfaces*).—Glabrous.
- *Leaf attachment.*—Petiolate.
- *Leaf fragrance.*—None observed.
- *Petiole shape.*—Sulcate.
- *Petiole dimensions.*—2.50 cm to 4 cm in length and 0.10 cm in width.
- *Petiole color.*—N186B.
- *Presence of stipules or spines.*—None observed.

Inflorescence:
- *Inflorescence type.*—Head.
- *Aspect.*—Facing upward and outward.
- *Inflorescence quantity.*—15–20 per 2-liter container plant.
- *Dimensions of inflorescence* (*average*).—9 cm in diameter and 6.50 cm in depth.
- *Inflorescence shape.*—Radiate with center disc.
- *Blooming seasons.*—Summer and fall.
- *Peduncle.*—Dimensions (average): 10 cm in length and 0.40 cm. in diameter. Shape: Cylindrical. Surface: Glabrous. Color: N186B.
- *Bud.*—Shape: Oblate. Dimensions (average): 2 cm in height and 1.75 cm in diameter. Surface: Glabrous. Appearance: Semi-glossy. Color: 187A. Apex: Obtuse. Base: Truncate.
- *Ray florets.*—Quantity per inflorescence: 8. Dimensions (average): 4.50 cm. in length and 2.50 cm. in width. Form: Petaloid. Shape: Obovate. Surface (adaxial and abaxial): Glabrous. Arrangement: Radiate. Apex: Obtuse. Base: Cuneate. Margin: Entire. Color (adaxial and abaxial surfaces): 1A. Vein color (adaxial and abaxial surfaces): 187C. Vein pattern: Parallel.
- *Disk florets.*—Quantity of disk florets: In excess of 90 per inflorescence. Dimensions: 1.75 cm in length and 0.10 cm in width. Color: 187A. Disk florets: 8 in number. Disk florets fused or unfused: Fused. Disk floret apex: Acute. Disk floret surface (ventral and dorsal surfaces): Glabrous. Receptacle dimensions: 1 cm in depth and 1.60 cm in diameter. Receptacle surface: Glabrous. Receptacle color: 187A.
- *Phyllary.*—Inner phyllary: Number: 8. Shape: Elongated ovate. Dimensions: 2.50 cm in length and 0.7 cm in width. Color (adaxial and abaxial surfaces): N199B/N199C. Texture: Scarious. Appearance: Translucent. Apex: Subacute. Base: Truncate. Margin: Entire. Surface (adaxial and abaxial): Glabrous. Outer phyllary: Number: 5 in number. Shape: Obovate. Dimensions: 1.50 cm. in length and 0.75 cm. in width. Color (adaxial and abaxial surfaces): N187A and N189A both present. Form: Reflexed. Apex: Obtuse. Base: Truncate. Margin: Entire. Surface (adaxial and abaxial): Glabrous.
- *Self-cleaning or persistent.*—Self-cleaning.
- *Fragrance of inflorescence.*—Perfume fragrance.

Reproductive organs:
- *Stamens.*—5 in number.
- *Stamen attachment.*—Filament adnate to ventral surface of corolla.

*Stamen length.*—6 mm in length.
*Stamen color.*—166A.
*Anther.*—Connate.
*Anther color.*—166A.
*Pollen.*—Present.
*Quantity.*—Large amount.
*Pollen color.*—N163D.
*Pistil.*—One present.
*Pistil length.*—9 mm in length.
*Stigma dimensions.*—3 mm in length and 4.50 mm in width.
*Stigma form.*—Plumose.
*Stigma color.*—N163A.
*Stigma shape.*—Bifurcate.
*Ovary position.*—Inferior.
*Ovary color.*—150D.
*Ovary shape.*—Rotund.
*Ovary dimensions.*—2 mm in width and 3 mm in height.

Seed: None observed to date.

It is claimed:

1. A new and distinct cultivar of *Dahlia* plant named 'KNOCKOUT' as described and illustrated herein.

* * * * *